(12) United States Patent
Lassen

(10) Patent No.: US 10,207,974 B1
(45) Date of Patent: Feb. 19, 2019

(54) SYNTHESIS OF GAMMA DICARBONYL AND PYRROLE COMPOUNDS

(71) Applicant: Chevron Phillips Chemical Company LP, The Woodlands, TX (US)

(72) Inventor: Kenneth M. Lassen, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 15/831,430

(22) Filed: Dec. 5, 2017

(51) Int. Cl.
| | |
|---|---|
| C07C 45/61 | (2006.01) |
| C07C 45/72 | (2006.01) |
| C07D 207/32 | (2006.01) |
| C07C 45/78 | (2006.01) |
| C07C 49/12 | (2006.01) |
| C07B 37/02 | (2006.01) |
| B01J 31/02 | (2006.01) |

(52) U.S. Cl.
CPC ........... *C07C 45/61* (2013.01); *C07B 37/02* (2013.01); *C07C 45/78* (2013.01); *C07C 49/12* (2013.01); *C07D 207/32* (2013.01); *B01J 31/0215* (2013.01); *B01J 31/0237* (2013.01); *B01J 31/0241* (2013.01); *B01J 31/0244* (2013.01)

(58) Field of Classification Search
CPC ........ C07C 45/61; C07C 45/72; C07D 207/32
See application file for complete search history.

(56) References Cited

U.S. PATENT DOCUMENTS

| | | | |
|---|---|---|---|
| 6,229,051 B1 | 5/2001 | Sandefur | |
| 6,258,959 B1 | 7/2001 | Gröning et al. | |
| 7,034,163 B2 | 4/2006 | Pagenkopf et al. | |
| 7,250,520 B2 | 7/2007 | Wallace | |
| 7,799,932 B2 | 9/2010 | Reynolds et al. | |
| 8,148,545 B2 | 4/2012 | Yang et al. | |
| 8,273,901 B2 | 9/2012 | Zhong et al. | |
| 8,362,278 B2 | 1/2013 | Kreischer et al. | |
| 8,729,277 B2 | 5/2014 | Yang et al. | |
| 9,266,831 B2 | 2/2016 | Ikemoto et al. | |
| 2012/0083608 A1 | 4/2012 | Fazekas et al. | |

OTHER PUBLICATIONS

Ballini, et al., entitled "Nitroalkanes in Aqueous Medium as an Efficient and Eco-Friendly Source for the One-Pot Synthesis of 1,4-Diketones, 1, 4-Diols, δ-Nitroalkanols, and Hydroxytetrahydrofurans," J. Org. Chem., 68, 9173-9176, 2003.

Ballini, et al., entitled "The Michael Reaction of Nitroalkanes with Conjugated Enones in Aqueous Media," Tetrahedron Letter, 37:44, 8027-8030, 1996.

Setter, et al., entitled "The Stetter Reaction: 2,5-Undecanedione and 3-Methyl-2-Pentyl-2-Cyclopenten-1-One," Org. Syn., Coll., vol. 8, p. 620, 1993.

Shaabani, et al., entitled "Solvent free permanganate oxidations," Tetrahedron Letter, 42:34, 5833-5836, 2001.

Yasuda, et al., entitled "Synthesis of 1,4-Diketones: Unusual Coupling of Tin Enolates with α-Chloro Ketones Catalyzed by Zinc Halides," J. Org. Chem., 62, 8282-8283, 1997.

Young, et al., entitled "2,5-Dimethylpyrrole," Org. Syn., Coll., vol. 2, p. 219, 1943.

*Primary Examiner* — Sikarl A Witherspoon
(74) *Attorney, Agent, or Firm* — Merchant & Gould P.C.

(57) ABSTRACT

The present invention discloses processes for producing γ-dicarbonyl compounds by contacting an aldehyde compound, an α,β-unsaturated carbonyl compound, and a catalyst composition in the presence of an amide diluent. The resultant γ-dicarbonyl compounds then can be used to synthesize pyrrole compounds, such as 2,5-dimethylpyrrole.

20 Claims, 2 Drawing Sheets

SYNTHESIS OF GAMMA DICARBONYL AND PYRROLE COMPOUNDS

FIELD OF THE INVENTION

The present disclosure concerns processes for producing γ-dicarbonyl compounds as a precursor to pyrrole compounds. More particularly, the present disclosure relates to contacting an aldehyde compound with an α,β-unsaturated carbonyl compound to form γ-dicarbonyl compounds, and to the use of certain catalyst compositions and amide diluents for producing such γ-dicarbonyl compounds.

BACKGROUND OF THE INVENTION

Pyrrole compounds, such as 2,5-dimethylpyrrole, can be used as components in oligomerization catalyst systems for producing α-olefin oligomers, such as 1-hexene or 1-octene, from ethylene. However, the synthesis schemes to produce pyrrole compounds and their γ-dicarbonyl precursors often suffer from one or more of low yield, large by-product formation, and difficult isolation and purification of the desired γ-dicarbonyl precursor compounds. Accordingly, the present invention is generally directed to a synthesis scheme to produce γ-dicarbonyl compounds that overcomes these noted deficiencies.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Processes for producing a γ-dicarbonyl compound having formula (I),

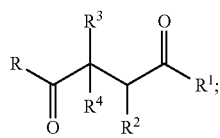
(I)

are disclosed herein. In accordance with an aspect of the present invention, one such process can comprise contacting (a) an aldehyde compound having formula (II),

(II)

(b) an α,β-unsaturated carbonyl compound having formula (III),

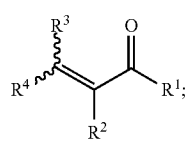
(III)

and
(c) a catalyst composition; in an amide diluent to produce the γ-dicarbonyl compound. In these formulas, R, $R^1$, $R^2$, $R^3$, and $R^4$ independently can be H, a halide, a $C_1$ to $C_{36}$ hydrocarbyl group, a $C_1$ to $C_{36}$ hydrocarboxy group, a $C_1$ to $C_{36}$ halogenated hydrocarbyl group, a $C_1$ to $C_{36}$ hydrocarbylaminyl group, a $C_1$ to $C_{36}$ hydrocarbylsilyl group, or a $C_1$ to $C_{36}$ hydrocarbylaminylsilyl group.

Processes for producing a pyrrole compound having formula (IV),

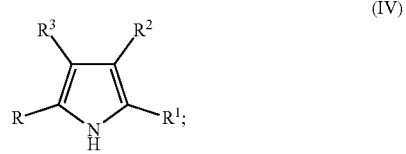
(IV)

also are disclosed herein. In certain aspects, the process can comprise (1) contacting (a) an aldehyde compound having formula (II),

(II)

(b) an α,β-unsaturated carbonyl compound having formula (III),

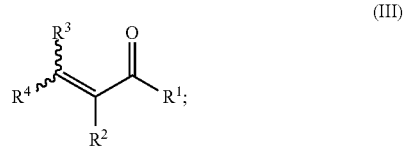
(III)

and
(c) a catalyst composition; in an amide diluent to produce a γ-dicarbonyl compound having formula (I),

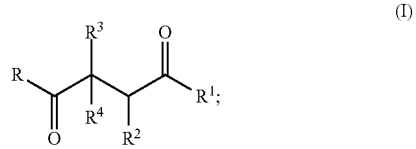
(I)

and
(2) contacting the γ-dicarbonyl compound with ammonia or an ammonium salt to produce the pyrrole compound. In these formulas, $R^4$ can be H, and R, $R^1$, $R^2$, and $R^3$ independently can be H, a halide, a $C_1$ to $C_{36}$ hydrocarbyl group, a $C_1$ to $C_{36}$ hydrocarboxy group, a $C_1$ to $C_{36}$ halogenated hydrocarbyl group, a $C_1$ to $C_{36}$ hydrocarbylaminyl group, a $C_1$ to $C_{36}$ hydrocarbylsilyl group, or a $C_1$ to $C_{36}$ hydrocarbylaminylsilyl group.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

BRIEF DESCRIPTION OF THE FIGURES

The following figures form part of the present specification and are included to further demonstrate certain aspects of the present invention. The invention may be better understood by reference to one or more of these figures in combination with the detailed description and examples.

DEFINITIONS

Figure 1:
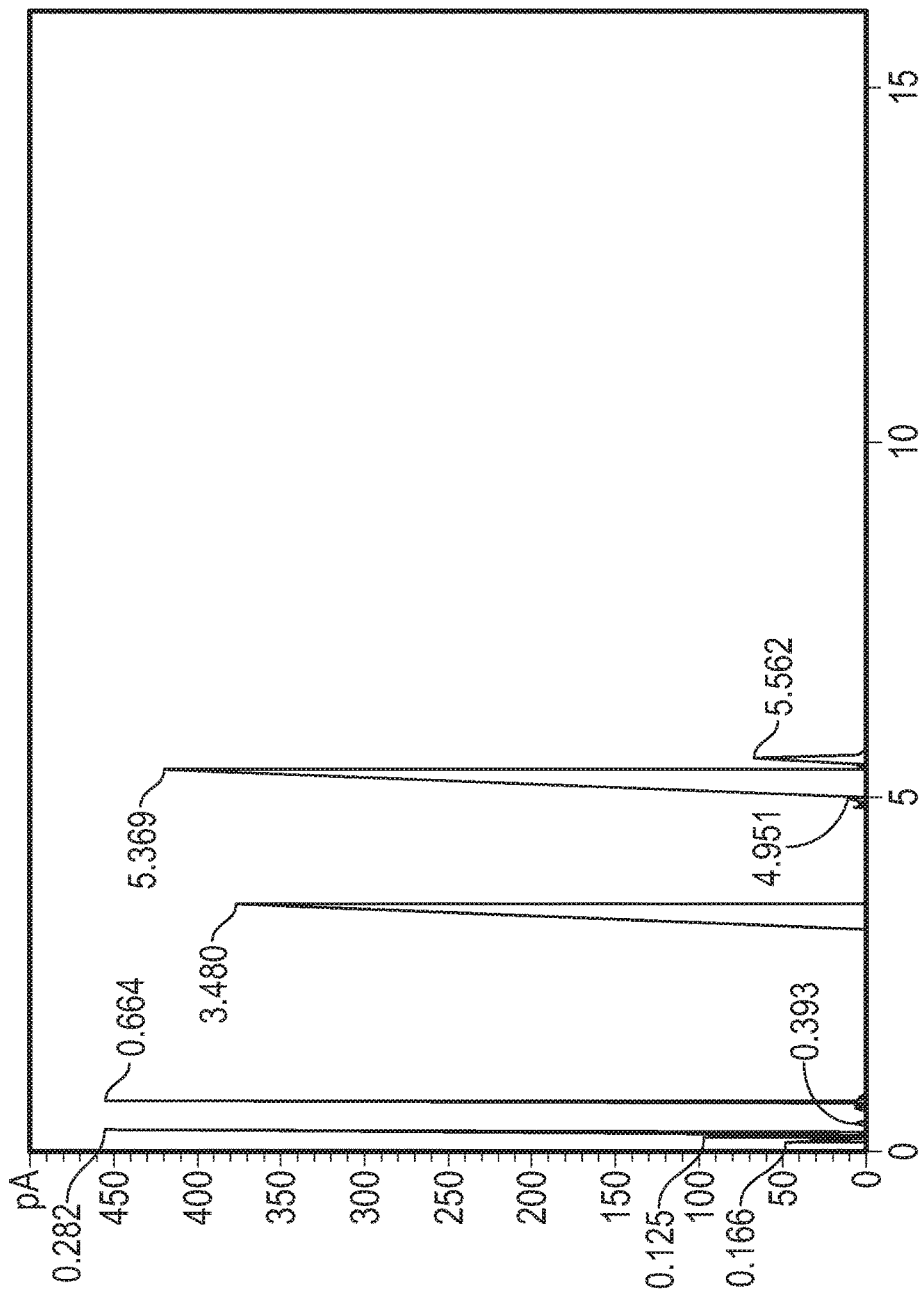
FIG. 1 presents a gas chromatograph plot of the crude product mixture of Example 1 containing 2,5-hexanedione.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the compounds, compositions, processes, or methods described herein are contemplated with or without explicit description of the particular combination. Additionally, unless explicitly recited otherwise, any aspect or feature disclosed herein can be combined to describe inventive compounds, compositions, processes, or methods consistent with the present disclosure.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

As used herein, the term "$\alpha,\beta$-unsaturated carbonyl compound" refers to an aldehyde or ketone having a carbon atom of a carbon-carbon double bond attached to the carbonyl carbon atom (the carbon atom bearing the double bonded oxygen atom of the aldehyde or ketone group). While the $\alpha,\beta$-unsaturated carbonyl compound must minimally contain at least the two groups having the designated relationship, the compounds can contain additional carbon-carbon double bonds, aldehyde groups, and/or ketone groups, which may or may not have the designated relationship. Additionally, unless otherwise specified, the $\alpha,\beta$-unsaturated carbonyl compound can contain other heteroatoms and/or functional groups (e.g., ester or amide groups).

In like manner, the term "$\gamma$-dicarbonyl compound" refers to a compound having two ketone groups, two aldehyde groups, or an aldehyde group and a ketone group, separated by two contiguous carbon atoms. While the $\gamma$-dicarbonyl compound must contain at least the two groups in the designated relationship, these compounds can contain additional aldehyde and/or ketone groups, which may or may not have the designated relationship. Additionally, unless otherwise specified, the $\gamma$-dicarbonyl compound can contain other heteroatoms and/or functional groups (e.g., ester or amide groups).

The term "hydrocarbon" whenever used in this specification and claims refers to a compound containing only carbon and hydrogen, whether saturated or unsaturated. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon (that is, a group containing only carbon and hydrogen). Non-limiting examples of hydrocarbyl groups include alkyl, alkenyl, aryl, and aralkyl groups, amongst other groups.

For any particular compound or group disclosed herein, any name or structure (general or specific) presented is intended to encompass all conformational isomers, regioisomers, stereoisomers, and mixtures thereof that can arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. For instance, a general reference to pentane includes n-pentane, 2-methyl-butane, and 2,2-dimethylpropane; and a general reference to a butyl group includes a n-butyl group, a sec-butyl group, an iso-butyl group, and a t-butyl group.

Unless otherwise specified, the term "substituted" when used to describe a group, for example, when referring to a substituted analog of a particular group, is intended to describe any non-hydrogen moiety that formally replaces a hydrogen in that group, and is intended to be non-limiting. Also, unless otherwise specified, a group or groups can also be referred to herein as "unsubstituted" or by equivalent terms such as "non-substituted," which refers to the original group in which a non-hydrogen moiety does not replace a hydrogen within that group. Moreover, unless otherwise specified, "substituted" is intended to be non-limiting and include inorganic substituents or organic substituents as understood by one of ordinary skill in the art.

The terms "contact product," "contacting," and the like, are used herein to describe methods and compositions wherein the components are contacted together in any order, in any manner, and for any length of time, unless otherwise specified. For example, the components can be contacted by blending or mixing. Further, unless otherwise specified, the contacting of any component can occur in the presence or absence of any other component of the methods and compositions described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Consequently, depending upon the circumstances, a "contact product" can be a mixture, a reaction mixture, or a reaction product. Likewise, "contacting" two or more components can result in a reaction product or a reaction mixture.

In this disclosure, while compositions and processes are described in terms of "comprising" various components or steps, the compositions and processes can also "consist essentially of" or "consist of" the various components or steps, unless stated otherwise.

The terms "a," "an," and "the" are intended to include plural alternatives, e.g., at least one. For instance, the disclosure of "a base," "an aldehyde compound," "a γ-dicarbonyl compound," etc., is meant to encompass one, or mixtures or combinations of more than one, base, aldehyde compound, γ-dicarbonyl compound, etc., unless otherwise specified.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, when a chemical moiety having a certain number of carbon atoms is disclosed or claimed, the intent is to disclose or claim individually every possible number that such a range could encompass, consistent with the disclosure herein. For example, the disclosure that a moiety is a $C_1$ to $C_{18}$ hydrocarbyl group, or in alternative language, a hydrocarbyl group having from 1 to 18 carbon atoms, as used herein, refers to a moiety that can have 1, 2, 3, 4, 5, 6, 7, 8, 9, 10, 11, 12, 13, 14, 15, 16, 17, or 18 carbon atoms, as well as any range between these two numbers (for example, a $C_1$ to $C_8$ hydrocarbyl group), and also including any combination of ranges between these two numbers (for example, a $C_2$ to $C_4$ and a $C_{12}$ to $C_{16}$ hydrocarbyl group).

Similarly, another representative example follows for the volumetric ratio of the amide diluent to the α,β-unsaturated carbonyl compound consistent with aspects of this invention. By a disclosure that the volumetric ratio of the amide diluent to the α,β-unsaturated carbonyl compound can be in a range from about 1:2 to about 10:1, the intent is to recite that the ratio can be any ratio in the range and, for example, can be equal to about 1:2, about 1:1, about 2:1, about 3:1, about 4:1, about 5:1, about 6:1, about 7:1, about 8:1, about 9:1, or about 10:1. Additionally, the volumetric ratio can be within any range from about 1:2 to about 10:1 (for example, from about 1:2 to about 5:1), and this also includes any combination of ranges between about 1:2 and about 10:1 (for example, the ratio can be in a range from about 1:1.5 to about 1.5:1, or from about 3:1 to about 8:1). Likewise, all other ranges disclosed herein should be interpreted in a manner similar to these examples.

The term "about" means that amounts, sizes, formulations, parameters, and other quantities and characteristics are not and need not be exact, but may be approximate including being larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, and often within 5% of the reported numerical value.

All disclosed product yields are based on the limiting reactant in the respective reaction, unless explicitly stated otherwise. For example, the limiting reactant in a process for synthesizing a γ-dicarbonyl compound can be an α,β-unsaturated carbonyl compound and, therefore, the yield of the γ-dicarbonyl compound would be based on the initial quantity of the α,β-unsaturated carbonyl compound.

Although any methods, devices, and materials similar or equivalent to those described herein can be used in the practice or testing of the invention, the typical methods, devices, and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

Disclosed herein are processes for producing γ-dicarbonyl compounds by contacting an aldehyde compound and an α,β-unsaturated carbonyl compound with a catalyst composition. Advantageously, when these processes are conducted in the presence of an amide diluent, these processes can result in a greater conversion of the aldehyde and carbonyl compounds, and a reduction in by-products. Thus, surprisingly, the processes disclosed herein can produce γ-dicarbonyl compounds in higher yields and of higher purity when conducted in the presence of an amide diluent.

The γ-dicarbonyl compounds produced in accordance with this disclosure can be used to synthesize pyrrole compounds which, subsequently, can be used as a component of an olefin oligomerization catalyst system.

Synthesizing Gamma Dicarbonyl Compounds

Aspects of this invention are directed to a process to produce a γ-dicarbonyl compound. For instance, a process for producing a γ-dicarbonyl compound having formula (I),

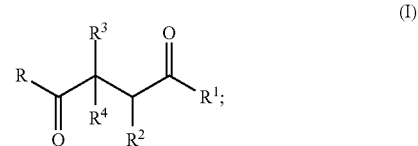

consistent with this invention can comprise (or consist essentially of, or consist of) contacting:

(a) an aldehyde compound having formula (II),

(b) an α,β-unsaturated carbonyl compound having formula (III),

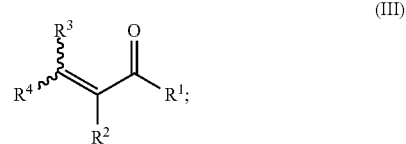

and
(c) a catalyst composition; in an amide diluent to produce the γ-dicarbonyl compound.

Generally, the features of this process for producing a dicarbonyl compound (e.g., the aldehyde compound, the unsaturated carbonyl compound, the catalyst composition, the amide diluent, and the conditions under which the dicarbonyl compound is formed, among others) are independently described herein and these features can be combined in any combination to further describe the disclosed process to produce a dicarbonyl compound. Moreover, additional process steps can be performed before, during, and/or after the contacting/reacting step of this process, and can be utilized without limitation and in any combination to further describe the dicarbonyl synthesis process, unless stated otherwise.

Formulas (I), (II), and (III) are not designed to show stereochemistry or isomeric positioning of the different moieties (e.g., these formulas are not intended to show cis or trans isomers), although such compounds are contemplated and encompassed by these formulas. In these formulas, R, $R^1$, $R^2$, $R^3$, and $R^4$ independently can be H, a halide, a $C_1$ to $C_{36}$ hydrocarbyl group, a $C_1$ to $C_{36}$ hydrocarboxy group, a $C_1$ to $C_{36}$ halogenated hydrocarbyl group, a $C_1$ to $C_{36}$ hydrocarbylaminyl group, a $C_1$ to $C_{36}$ hydrocarbylsilyl group, or a $C_1$ to $C_{36}$ hydrocarbylaminylsilyl group. It is contemplated that any of R, $R^1$, $R^2$, $R^3$, and $R^4$ can be the same or different.

In one aspect, for instance, R, $R^1$, $R^2$, $R^3$, and $R^4$ independently can be H, a halide, a $C_1$ to $C_{18}$ hydrocarbyl group, a $C_1$ to $C_{18}$ hydrocarboxy group, a $C_1$ to $C_{18}$ halogenated hydrocarbyl group, a $C_1$ to $C_{18}$ hydrocarbylaminyl group, a $C_1$ to $C_{18}$ hydrocarbylsilyl group, or a $C_1$ to $C_{18}$ hydrocarbylaminylsilyl group. In another aspect, R, $R^1$, $R^2$, $R^3$, and $R^4$ independently can be H, a halide, a $C_1$ to $C_{12}$ hydrocarbyl group, a $C_1$ to $C_{12}$ hydrocarboxy group, a $C_1$ to $C_{12}$ halogenated hydrocarbyl group, a $C_1$ to $C_{12}$ hydrocarbylaminyl group, a $C_1$ to $C_{12}$ hydrocarbylsilyl group, or a $C_1$ to $C_{12}$ hydrocarbylaminylsilyl group. In yet another aspect, R, $R^1$, $R^2$, $R^3$, and $R^4$ independently can be H, a halide, a $C_1$ to $C_8$ hydrocarbyl group, a $C_1$ to $C_8$ hydrocarboxy group, a $C_1$ to $C_8$ halogenated hydrocarbyl group, a $C_1$ to $C_8$ hydrocarbylaminyl group, a $C_1$ to $C_8$ hydrocarbylsilyl group, or a $C_1$ to $C_8$ hydrocarbylaminylsilyl group. In still another aspect, R, $R^1$, $R^2$, $R^3$, and $R^4$ independently can be H, a $C_1$ to $C_{18}$ hydrocarbyl group, a $C_1$ to $C_{18}$ hydrocarboxy group, or a $C_1$ to $C_{18}$ halogenated hydrocarbyl group, or alternatively, R, $R^1$, $R^2$, $R^3$, and $R^4$ independently can be H or a $C_1$ to $C_{18}$ hydrocarbyl group. As an example, R, $R^1$, $R^2$, $R^3$, and $R^4$ independently can be H or a $C_1$ to $C_{18}$ alkyl, aryl, or arylalkyl group.

In these and other aspects, $R^4$ can be H, while R, $R^1$, $R^2$, and $R^3$ independently can be any group described herein. In a further aspect, R and $R^1$ independently can be a $C_1$ to $C_{18}$ hydrocarbyl group, and $R^2$ and $R^3$ can be hydrogen.

R, $R^1$, $R^2$, $R^3$, and $R^4$ independently can be H or a $C_1$ to $C_{18}$ hydrocarbyl group in certain aspects of this invention. For instance, R, $R^1$, $R^2$, $R^3$, and $R^4$ in formula (I) independently can be a $C_1$ to $C_{18}$ alkyl group, a $C_2$ to $C_{18}$ alkenyl group, a $C_4$ to $C_{18}$ cycloalkyl group, a $C_6$ to $C_{18}$ aryl group, or a $C_7$ to $C_{18}$ aralkyl group; alternatively, R, $R^1$, $R^2$, $R^3$, and $R^4$ independently can be a $C_1$ to $C_{12}$ alkyl group, a $C_2$ to $C_{12}$ alkenyl group, a $C_4$ to $C_{12}$ cycloalkyl group, a $C_6$ to $C_{12}$ aryl group, or a $C_7$ to $C_{12}$ aralkyl group; alternatively, R, $R^1$, $R^2$, $R^3$, and $R^4$ independently can be a $C_1$ to $C_{10}$ alkyl group, a $C_2$ to $C_{10}$ alkenyl group, a $C_4$ to $C_{10}$ cycloalkyl group, a $C_6$ to $C_{10}$ aryl group, or a $C_7$ to $C_{10}$ aralkyl group; or alternatively, R, $R^1$, $R^2$, $R^3$, and $R^4$ independently can be a $C_1$ to $C_5$ alkyl group, a $C_2$ to $C_5$ alkenyl group, a $C_5$ to $C_8$ cycloalkyl group, a $C_6$ to $C_8$ aryl group, or a $C_7$ to $C_8$ aralkyl group.

Accordingly, in some aspects, the alkyl group which can be any of R, $R^1$, $R^2$, $R^3$, and $R^4$ in formula (I) can be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, or an octadecyl group; or alternatively, a methyl group, an ethyl group, a propyl group, a butyl group, a pentyl group, a hexyl group, a heptyl group, an octyl group, a nonyl group, or a decyl group. In some aspects, the alkyl group which can be any of R, $R^1$, $R^2$, $R^3$, and $R^4$ in formula (I) can be a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, a n-propyl group; alternatively, an iso-propyl group; alternatively, a tert-butyl group; or alternatively, a neopentyl group. Thus, R, $R^1$, $R^2$, $R^3$, and $R^4$ independently can be H or a $C_1$ to $C_8$ alkyl group.

Suitable alkenyl groups which can be any of R, $R^1$, $R^2$, $R^3$, and $R^4$ in formula (I) can include, but are not limited to, an ethenyl group, a propenyl group, a butenyl group, a pentenyl group, a hexenyl group, a heptenyl group, an octenyl group, a nonenyl group, a decenyl group, a undecenyl group, a dodecenyl group, a tridecenyl group, a tetradecenyl group, a pentadecenyl group, a hexadecenyl group, a heptadecenyl group, or an octadecenyl group. Such alkenyl groups can be linear or branched, and the double bond can be located anywhere in the chain. For example, in some aspects, at least one of R, $R^1$, $R^2$, $R^3$, and $R^4$ can be a $C_3$ to $C_{12}$ alkenyl group, or a $C_3$ to $C_{12}$ terminal alkenyl group.

Any of R, $R^1$, $R^2$, $R^3$, and $R^4$ in formula (I) independently can be a cycloalkyl group, including, but not limited to, a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. Substituents which can be utilized for the substituted cycloalkyl group are independently disclosed herein and can be utilized without limitation to further describe the substituted cycloalkyl group which can be any of R, $R^1$, $R^2$, $R^3$, and $R^4$ in formula (I).

In some aspects, the aryl group which can be any of R, $R^1$, $R^2$, $R^3$, and $R^4$ in formula (I) can be a phenyl group, a substituted phenyl group, a naphthyl group, or a substituted naphthyl group. In an aspect, the aryl group can be a phenyl group or a substituted phenyl group; alternatively, a naphthyl group or a substituted naphthyl group; alternatively, a phenyl group or a naphthyl group; alternatively, a substituted phenyl group or a substituted naphthyl group; alternatively, a phenyl group; or alternatively, a naphthyl group. Substituents which can be utilized for the substituted phenyl groups or substituted naphthyl groups are independently disclosed herein and can be utilized without limitation to further describe the substituted phenyl groups or substituted naphthyl groups which can be any of R, $R^1$, $R^2$, $R^3$, and $R^4$ in formula (I).

In an aspect, the substituted phenyl group which can be any of R, $R^1$, $R^2$, $R^3$, and $R^4$ in formula (I) can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group. In other aspects, the substituted phenyl group can be a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. Substituents which can be utilized for these specific substituted phenyl groups are independently disclosed herein and can be utilized without limitation to further describe these substituted phenyl groups which can be any of R, $R^1$, $R^2$, $R^3$, and $R^4$ in formula (I).

In some aspects, the aralkyl group which can be any of R, $R^1$, $R^2$, $R^3$, and $R^4$ in formula (I) can be a benzyl group or a substituted benzyl group. In an aspect, the aralkyl group can be a benzyl group or, alternatively, a substituted benzyl group. Substituents which can be utilized for the substituted aralkyl group are independently disclosed herein and can be utilized without limitation to further describe the substituted aralkyl group which can be any of R, $R^1$, $R^2$, $R^3$, and $R^4$ in formula (I).

In an aspect, each non-hydrogen substituent(s) for the substituted cycloalkyl group, substituted aryl group, or substituted aralkyl group which can be any of R, $R^1$, $R^2$, $R^3$, and $R^4$ in formula (I) independently can be a $C_1$ to $C_{18}$ hydrocarbyl group; alternatively, a $C_1$ to $C_8$ hydrocarbyl group; or alternatively, a $C_1$ to $C_5$ hydrocarbyl group. Specific hydrocarbyl groups are independently disclosed herein and can be utilized without limitation to further describe the substituents of the substituted cycloalkyl groups, substituted aryl groups, or substituted aralkyl groups, which can be any of R, $R^1$, $R^2$, $R^3$, and $R^4$ in formula (I). For instance, the hydrocarbyl substituent can be an alkyl group, such as a methyl group, an ethyl group, a n-propyl group, an isopropyl group, a n-butyl group, a sec-butyl group, an isobutyl group, a tert-butyl group, a n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group, and the like. Furthermore, the hydrocarbyl substituent can be a benzyl group, a phenyl group, a tolyl group, or a xylyl group, and the like.

Accordingly, in certain aspects, R and $R^1$ independently can be a methyl group, an ethyl group, an n-propyl group, an iso-propyl group, an n-butyl group, a t-butyl group, a phenyl group, a benzyl group, a tolyl group, or a xylyl group. In one aspect, for instance, R can be a methyl group, while in another aspect, R and $R^1$ can be a methyl group, and $R^2$ and $R^3$ can be hydrogen.

Further, any of R, $R^1$, $R^2$, $R^3$, and $R^4$ in formula (I) independently can be, in certain aspects, a $C_1$ to $C_{36}$ halogenated hydrocarbyl group, where the halogenated hydrocarbyl group indicates the presence of one or more halogen atoms replacing an equivalent number of hydrogen atoms in the hydrocarbyl group. The halogenated hydrocarbyl group often can be a halogenated alkyl group, a halogenated alkenyl group, a halogenated cycloalkyl group, a halogenated aryl group, or a halogenated aralkyl group. Representative and non-limiting halogenated hydrocarbyl groups include pentafluorophenyl, trifluoromethyl ($CF_3$), and the like.

A hydrocarboxy group is used generically herein to include, for instance, alkoxy, aryloxy, aralkoxy, -(alkyl, aryl, or aralkyl)-O-(alkyl, aryl, or aralkyl) groups, and —O(CO)-(hydrogen or hydrocarbyl) groups, and these groups can comprise up to about 36 carbon atoms (e.g., $C_1$ to $C_{36}$, $C_1$ to $C_{18}$, $C_1$ to $C_{10}$, or $C_1$ to $C_8$ hydrocarboxy groups). Illustrative and non-limiting examples of hydrocarboxy groups which can be any of R, $R^1$, $R^2$, $R^3$, and $R^4$ in formula (I) can include, but are not limited to, a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, a neo-pentoxy group, a phenoxy group, a toloxy group, a xyloxy group, a 2,4,6-trimethylphenoxy group, a benzoxy group, an acetylacetonate group (acac), a formate group, an acetate group, a stearate group, an oleate group, a benzoate group, and the like. In an aspect, the hydrocarboxy group which can be any of R, $R^1$, $R^2$, $R^3$, and $R^4$ in formula (I) can be a methoxy group; alternatively, an ethoxy group; alternatively, an n-propoxy group; alternatively, an iso-propoxy group; alternatively, an n-butoxy group; alternatively, a sec-butoxy group; alternatively, an isobutoxy group; alternatively, a tert-butoxy group; alternatively, an n-pentoxy group; alternatively, a 2-pentoxy group; alternatively, a 3-pentoxy group; alternatively, a 2-methyl-1-butoxy group; alternatively, a tert-pentoxy group; alternatively, a 3-methyl-1-butoxy group, alternatively, a 3-methyl-2-butoxy group; alternatively, a neo-pentoxy group; alternatively, a phenoxy group; alternatively, a toloxy group; alternatively, a xyloxy group; alternatively, a 2,4,6-trimethylphenoxy group; alternatively, a benzoxy group; alternatively, an acetylacetonate group; alternatively, a formate group; alternatively, an acetate group; alternatively, a stearate group; alternatively, an oleate group; or alternatively, a benzoate group.

In accordance with some aspects disclosed herein, any of R, $R^1$, $R^2$, $R^3$, and $R^4$ in formula (I) can be a $C_1$ to $C_{36}$ hydrocarbylaminyl group; alternatively, a $C_1$ to $C_{24}$ hydrocarbylaminyl group; alternatively, a $C_1$ to $C_{18}$ hydrocarbylaminyl group; or alternatively, a $C_1$ to $C_8$ hydrocarbylaminyl group. The term hydrocarbylaminyl group is used generically herein to refer collectively to, for instance, alkylaminyl, arylaminyl, aralkylaminyl, dialkylaminyl, diarylaminyl, diaralkylaminyl, and -(alkyl, aryl, or aralkyl)-N-(alkyl, aryl, or aralkyl) groups, and unless otherwise specified, the hydrocarbylaminyl groups which can be any of R, $R^1$, $R^2$, $R^3$, and $R^4$ in formula (I) can comprise up to about 36 carbon atoms (e.g., $C_1$ to $C_{36}$, $C_1$ to $C_{18}$, $C_1$ to $C_{10}$, or $C_1$ to $C_8$ hydrocarbylaminyl groups). Accordingly, hydrocarbylaminyl is intended to cover both (mono)hydrocarbylaminyl and dihydrocarbylaminyl groups. In some aspects, the hydrocarbylaminyl group which can be any of R, $R^1$, $R^2$, $R^3$, and $R^4$ in formula (I) can be, for instance, a methylaminyl group (—$NHCH_3$), an ethylaminyl group (—$NHCH_2CH_3$), an n-propylaminyl group (—$NHCH_2CH_2CH_3$), an iso-propylaminyl group (—$NHCH(CH_3)_2$), an n-butylaminyl group (—$NHCH_2CH_2CH_2CH_3$), a t-butylaminyl group (—$NHC(CH_3)_3$), an n-pentylaminyl group (—$NHCH_2CH_2CH_2CH_2CH_3$), a neo-pentylaminyl group (—$NHCH_2C(CH_3)_3$), a phenylaminyl group (—$NHC_6H_5$), a tolylaminyl group (—$NHC_6H_4CH_3$), or a xylylaminyl group (—$NHC_6H_3(CH_3)_2$); alternatively, a methylaminyl group; alternatively, an ethylaminyl group; alternatively, a propylaminyl group; or alternatively, a phenylaminyl group. In other aspects, the hydrocarbylaminyl group which can be any of R, $R^1$, $R^2$, $R^3$, and $R^4$ in formula (I) can be, for instance, a dimethylaminyl group (—$N(CH_3)_2$), a diethylaminyl group (—$N(CH_2CH_3)_2$), a di-n-propylaminyl group (—$N(CH_2CH_2CH_3)_2$), a di-iso-propylaminyl group (—$N(CH(CH_3)_2)_2$), a di-n-butylaminyl group (—$N(CH_2CH_2CH_2CH_3)_2$), a di-t-butylaminyl group (—$N(C(CH_3)_3)_2$), a di-n-pentylaminyl group (—$N(CH_2CH_2CH_2CH_2CH_3)_2$), a di-neo-pentylaminyl group (—$N(CH_2C(CH_3)_3)_2$), a di-phenylaminyl group (—$N(C_6H_5)_2$), a di-tolylaminyl group (—$N(C_6H_4CH_3)_2$), or a di-xylylaminyl group (—$N(C_6H_3(CH_3)_2)_2$); alternatively, a dimethylaminyl group; alternatively, a di-ethylaminyl group; alternatively, a di-n-propylaminyl group; or alternatively, a di-phenylaminyl group.

Similarly, in other aspects, any of R, $R^1$, $R^2$, $R^3$, and $R^4$ in formula (I) can be a $C_1$ to $C_{36}$ hydrocarbylaminylsilyl group; alternatively, a $C_1$ to $C_{24}$ hydrocarbylaminylsilyl group; alternatively, a $C_1$ to $C_{18}$ hydrocarbylaminylsilyl group; or alternatively, a $C_1$ to $C_8$ hydrocarbylaminylsilyl group. A hydrocarbylaminylsilyl group is used herein to refer to groups containing at least one hydrocarbon moiety, at least one N atom, and at least one Si atom.

Illustrative and non-limiting examples of hydrocarbylaminylsilyl groups which can be any of R, $R^1$, $R^2$, $R^3$, and $R^4$ in formula (I) can include, but are not limited to, —$N(SiMe_3)_2$, —$N(SiEt_3)_2$, and the like. Unless otherwise specified, the hydrocarbylaminylsilyl groups can comprise up to about 36 carbon atoms (e.g., $C_1$ to $C_{36}$, $C_1$ to $C_{18}$, $C_1$ to $C_{12}$, or $C_1$ to $C_8$ hydrocarbylaminylsilyl groups). In an aspect, each hydrocarbyl (one or more) of the hydrocarbylaminylsilyl group can be any hydrocarbyl group disclosed herein (e.g., a $C_1$ to $C_5$ alkyl group, a $C_2$ to $C_5$ alkenyl group, a $C_5$ to $C_8$ cycloalkyl group, a $C_6$ to $C_8$ aryl group, a $C_7$ to $C_8$ aralkyl group, etc.). Moreover, hydrocarbylaminylsilyl is intended to cover —$NH(SiH_2R)$, —$NH(SiHR_2)$, —$NH(SiR_3)$, —$N(SiH_2R)_2$, —$N(SiHR_2)_2$, and —$N(SiR_3)_2$ groups, among others, with R being a hydrocarbyl group.

In accordance with some aspects disclosed herein, any of R, $R^1$, $R^2$, $R^3$, and $R^4$ in formula (I) can be a $C_1$ to $C_{36}$ hydrocarbylsilyl group; alternatively, a $C_1$ to $C_{24}$ hydrocarbylsilyl group; alternatively, a $C_1$ to $C_{18}$ hydrocarbylsilyl group; or alternatively, a $C_1$ to $C_8$ hydrocarbylsilyl group. In an aspect, each hydrocarbyl (one or more) of the hydrocarbylsilyl group can be any hydrocarbyl group disclosed herein (e.g., a $C_1$ to $C_5$ alkyl group, a $C_2$ to $C_5$ alkenyl group, a $C_5$ to $C_8$ cycloalkyl group, a $C_6$ to $C_8$ aryl group, a $C_7$ to $C_8$ aralkyl group, etc.). As used herein, hydrocarbylsilyl is intended to cover (mono)hydrocarbylsilyl (—$SiH_2R$), dihydrocarbylsilyl (—$SiHR_2$), and trihydrocarbylsilyl (—$SiR_3$) groups, with R being a hydrocarbyl group. In one aspect, the hydrocarbylsilyl group can be a $C_3$ to $C_{36}$ or a $C_3$ to $C_{18}$ trihydrocarbylsilyl group, such as, for example, a trialkylsilyl group or a triphenylsilyl group. Illustrative and non-limiting examples of hydrocarbylsilyl groups which can be any of R, $R^1$, $R^2$, $R^3$, and $R^4$ in formula (I) can include, but are not limited to, trimethylsilyl, triethylsilyl, tripropylsilyl (e.g., triisopropylsilyl), tributylsilyl, tripentylsilyl, triphenylsilyl, allyldimethylsilyl, and the like.

Surprisingly, the processes to produce γ-dicarbonyl compounds contemplated herein can be particularly effective when the aldehyde compound, α,β-unsaturated carbonyl compound, and catalyst composition are contacted in the presence of an amide diluent. Thus, while the amide component is referred to as an amide "diluent," it can be an active participant in the reaction that produces the γ-dicarbonyl compound. While not wishing to be bound by theory, the improvements in reaction yield and purity observed in the presence of the amide diluent appear to go beyond simple concentration effects. Accordingly, the amide diluent may promote the reaction of the aldehyde compound with the α,β-unsaturated carbonyl compound, for instance, by stabilizing a transition state between the one or more reactants and a product or intermediate thereof. However, the amide diluent may increase the conversion of the aldehyde and unsaturated carbonyl compounds to the γ-dicarbonyl compound by any other means.

The chemical and/or physical properties of the amide diluent are not particularly limited to any specific compound; however, amide diluents with a boiling point different from the boiling point of the γ-dicarbonyl compound can prove advantageous during distillation and other separations processes in order to isolate the γ-dicarbonyl compound after the reaction. In certain aspects of the invention, the amide diluent can comprise a cyclic amide, a hydrocarbyl amide, or a combination thereof. One or more than amide diluent can be used in the processes disclosed herein. Similarly, the amide diluent can comprise a secondary amide, a tertiary amide, or a combination thereof. Accordingly, in certain aspects, suitable amide diluents can include, but are not limited to, pyrrolidone, N-methylpyrrolidone, acetamide, dimethylacetamide, dimethylformamide, benzamide, a lactam, and the like, as well as any combination thereof.

Likewise, the catalyst compositions used in the processes disclosed herein are not particularly limited, so long as they are able to promote a reaction between an aldehyde compound and an α,β-unsaturated carbonyl compound, as described herein. Illustrative and non-limiting catalyst compositions consistent with this invention can comprise an ylide species, a carbene species, a cyanide compound (e.g., sodium or potassium cyanide), and the like, as well as combinations thereof. In some aspects, the active species of the catalyst composition can be promoted by the presence of a base. Thus, in certain aspects contemplated herein, the catalyst composition can comprise a thiazolium compound that forms an ylide species in the presence of a base. Additional information on representative catalyst compositions is provided hereinbelow.

Generally, the appropriate procedure for the contacting (or reacting) step is not particularly limited. For instance, the step of contacting (or reacting) the aldehyde compound, the α,β-unsaturated carbonyl compound, and the catalyst composition in the amide diluent can comprise contacting the aldehyde compound, the α,β-unsaturated carbonyl compound, the catalyst composition, and the amide diluent in any order that produces an acceptable yield of the γ-dicarbonyl compound. Typically, the α,β-unsaturated carbonyl compound, the catalyst composition, and the amide diluent can be contacted first to form a reactant mixture, followed by contacting the aldehyde compound with the reactant mixture.

Certain ratios of components during the contacting steps can prove advantageous with respect to yield and purity of the γ-dicarbonyl compound. In one aspect, the molar ratio of the aldehyde compound to the α,β-unsaturated carbonyl compound can be greater than about 1:1, greater than about 1.2:1, greater than about 1.5:1, greater than about 2:1, greater than about 3:1, or greater than about 5:1. In such circumstances, the α,β-unsaturated carbonyl compound can be the limiting reactant in the process for producing the γ-dicarbonyl compound. Typical ranges for the molar ratio of the aldehyde compound to the α,β-unsaturated carbonyl compound can include, but are not limited to, from about 1:1 to about 5:1, from about 1:1 to about 2:1, from about 1.1:1 to about 2:1, from about 1.1:1 to about 1.8:1, or from about 1.2:1 about 1.6:1. It should be noted that an exorbitant excess of the aldehyde compound can promote undesirable side reactions.

Further, and unexpectedly, the volumetric ratio of the amide diluent to the α,β-unsaturated carbonyl compound can have a significant effect on the yield and purity of the crude γ-dicarbonyl compound. While not wishing to be bound by theory, if too little amide diluent is present, the aldehyde compound may convert more rapidly into unwanted by-products, whereas if the amide diluent is too prevalent, the conversion of the reactants to the γ-dicarbonyl compound may be reduced. Thus, in certain aspects of this invention, the volumetric ratio of the amide diluent to the α,β-unsaturated carbonyl compound can be in a range from about 1:1 to about 1:10, from about 1:2 to about 1:10; from about 1:1 to about 5:1, from about 1.5:1 to about 5:1, from about 1:2 to about 5:1, from about 1:2 to about 2:1, or from about 1:1.5 to about 1.5:1.

The processes to produce γ-dicarbonyl compound can be conducted at any suitable temperature and for any suitable period of time. Representative and non-limiting ranges for the temperature of the contacting step (or for the formation of the γ-dicarbonyl compound) can include from about −20° C. to about 70° C., from about 0° C. to about 50° C., from about 5° C. to about 60° C., or from about 15° C. to about 25° C. These temperature ranges also are meant to encompass circumstances where the contacting step (or the formation of the γ-dicarbonyl compound) is performed at a series of different temperatures, instead of at a single fixed temperature, falling within the respective temperature ranges.

Similarly, the time period for contacting the aldehyde compound, the α,β-unsaturated carbonyl compound, and the catalyst composition in the amide diluent (or for the formation of the γ-dicarbonyl compound) is not particularly limited, and can be conducted for any suitable period of time. In some aspects, the time period can be least about 1 minute, at least about 5 minutes, at least about 10 minutes, at least about 30 minutes, at least about 1 hour, at least about 2 hours, at least about 5 hours, or at least about 10 hours. In other aspects, the time period can be from about 30 seconds to about 48 hours, from about 1 minute to about 24 hours, from about 5 minutes to about 8 hours, from about 30 minutes to about 8 hours, or from about 1 hour to about 6 hours.

Unexpectedly, the processes described herein—which utilize an amide diluent—produce the γ-dicarbonyl compound in higher yield than that observed in analogous reactions using different diluents or solvents, or lacking a diluent altogether. Generally, the γ-dicarbonyl compound can be produced in a yield of at least about 25 mole %, and more often, at least about 40 mole %, at least about 50 mole %, at least about 60 mole %, or at least about 70 mole %, and often as high as 75-85 mole %. This yield is based on the moles of the limiting reactant, which is often the α,β-unsaturated carbonyl compound. Unless otherwise indicated, the compositional aspects of dicarbonyl products (or product mixtures containing dicarbonyl products) are disclosed in mole %. Any disclosure herein of a compositional aspect in mole % is also meant to encompass the same compositional aspect in area % (area percentage determined using a gas chromatograph, as described herein), because the disclosed processes and resultant products are often analyzed or evaluated in this manner. While not wishing to be bound by this theory, it is believed that the amount in area % is very similar to the amount in mole %, but these respective amounts are not identical or exactly interchangeable. In like manner, any disclosure herein of a compositional aspect in mole % is also meant to encompass the same compositional aspect in wt. %, because the respective amounts in wt. % are similar to those in mole %. As a representative example, a disclosure that the γ-dicarbonyl compound can be produced in a yield of at least about 50 mole % is meant also to disclose that the γ-dicarbonyl compound can be produced in a yield of at least about 50 area %, or the γ-dicarbonyl compound can be produced in a yield of at least about 50 wt. %, or both.

The processes to produce γ-dicarbonyl compounds disclosed herein typically result in a crude product mixture containing the γ-dicarbonyl compound and relatively minor amounts of impurities (e.g., condensed aldehyde, residual aldehyde, residual α,β-unsaturated carbonyl compound, catalyst composition components). Surprisingly, and advantageously, the use of the amide diluent in the processes described herein significantly reduces the amount of such impurities in the crude product mixture. Still, it can be useful to isolate the γ-dicarbonyl compound from the crude product mixture for use in further processes. Accordingly, in certain aspects, the process for producing a γ-dicarbonyl compound can further comprise a step of isolating the γ-dicarbonyl compound. Isolation of the γ-dicarbonyl compound can employ any suitable procedure for separating the γ-dicarbonyl compound from other components of the crude product mixture. The isolating step can comprise an extraction step, where the γ-dicarbonyl compound is selectively dissolved in an organic solvent. Alternatively, or additionally, the γ-dicarbonyl compound can be separated by distillation under atmospheric pressure or any suitable sub-atmospheric pressure.

After the isolating step, the isolated γ-dicarbonyl compound can have a purity of at least about 70 mole %, at least about 80 mole %, at least about 85 mole %, at least about 90 mole %, or at least about 95 mole %, and often as high as 98-99.5 mole % (as above, these same numerical values apply to corresponding values in area % and wt. %). Generally, purification steps to isolate a desired product from a crude mixture reduce the overall yield of the desired product. However, consistent with this invention, the isolated γ-dicarbonyl compound can be recovered in a yield similar to that of the crude γ-dicarbonyl compound. Thus the isolated γ-dicarbonyl compound can be recovered in a yield of at least about 25 mole %, and more often, at least about 40 mole %, at least about 50 mole %, at least about 60 mole %, or at least about 70 mole %, and often as high as 75-85 mole %. As above, this yield is based on the moles of the limiting reactant, which is often the α,β-unsaturated carbonyl compound, and these same numerical values apply to corresponding values in area % and wt. %.

Synthesizing Pyrrole Compounds

Aspects of this invention are directed to a process for producing a pyrrole compound.

This process can comprise (or consist essentially of, or consist of) the following steps:

(1) contacting:
(a) an aldehyde compound;
(b) an α,β-unsaturated carbonyl compound; and
(c) a catalyst composition;
in an amide diluent to produce a γ-dicarbonyl compound; and
(2) contacting the γ-dicarbonyl compound with ammonia or an ammonium salt to produce the pyrrole compound.

Generally, the features of this process for producing a pyrrole compound (e.g., the aldehyde compound, the unsaturated carbonyl compound, the catalyst composition, the amide diluent, the conditions under which the dicarbonyl compound is formed, and the conditions under which the pyrrole compound is formed, among others) are independently described herein and these features can be combined in any combination to further describe the disclosed process for producing a pyrrole compound. Moreover, additional process steps can be performed before, during, and/or after any of the steps of this process, and can be utilized without limitation and in any combination to further describe the pyrrole synthesis process, unless stated otherwise.

The first step of this process, the synthesis of γ-dicarbonyl compounds from aldehyde compounds and α,β-unsaturated carbonyl compounds, is discussed herein. Any aspects and features for producing the γ-dicarbonyl compounds described herein can be utilized in processes contemplated to produce the pyrrole compound and, accordingly, are encompassed by this invention.

For example, after step (1) of this process, the γ-dicarbonyl compound can be isolated from the reaction mixture using any suitable procedure. An extraction procedure with an organic solvent (e.g., a halogenated organic solvent) can be used. Additionally or alternatively, a distillation procedure at atmospheric pressure or any suitable sub-atmospheric pressure (e.g., 0.7 atm, 0.5 atm, 0.1 atm, or less than 0.1 atm) can be used. Subsequently, the isolated γ-dicarbonyl compound can be contacted with ammonia or an ammonium salt to produce the pyrrole compound. Alternatively, steps (1) and (2) of the process can be conducted in a single reactor. That is, this process can be a one-pot synthesis of a pyrrole compound from an aldehyde compound and an α,β-unsaturated carbonyl compound.

Step (2) of this process produces a pyrrole compound by contacting a γ-dicarbonyl compound with ammonia (e.g., liquid or gaseous ammonia) or an ammonium salt. This step of the process can be conducted in accordance with the general procedure for producing 2,5-dimethylpyrrole from 2,5-hexanedione described in Young et al., *Org. Syn. Coll.*, Vol. 2 (1943), p. 219, the disclosure of which is incorporated herein by reference in its entirety. Non-limiting examples of suitable ammonium salts that can be employed in this process include ammonium carbonate, ammonium acetate, and the like, or a combination thereof.

According to one aspect of this invention, the aldehyde compound can have the formula:

(II)

the α,β-unsaturated carbonyl compound can have the formula:

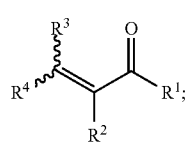
(III)

the γ-dicarbonyl compound can have the formula:

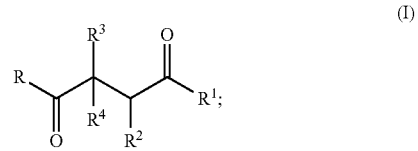
(I)

and
the pyrrole compound can have the formula:

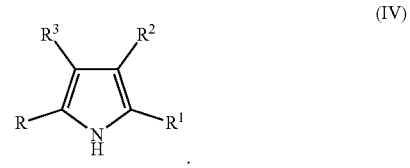
(IV)

As noted above, these formulas are not designed to show stereochemistry or isomeric positioning of the different moieties (e.g., these formulas are not intended to show cis or trans isomers), although such compounds are contemplated and encompassed by these formulas. R, $R^1$, $R^2$, and $R^3$ have been described herein and can be utilized without limitation to describe aspects of the method for synthesizing a pyrrole compound having formula (IV) utilizing the γ-dicarbonyl compound having formula (I). However, in the process for producing a pyrrole compound having formula (IV), $R^4$ is a hydrogen atom in formulas (I) and (III).

Catalyst Compositions

Catalyst compositions for the processes described herein can include any catalyst system that is suitable for the production of a dicarbonyl compound, as well as any combination of compounds that can give rise to an ylide species or carbene species (e.g., cyanide compounds can be used). An illustrative and non-limiting catalyst composition that can be utilized in the process disclosed herein can comprise a thiazolium compound having a formula (V):

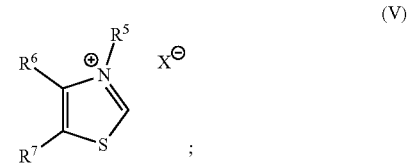
(V)

and a base.

In formula (V), X is not limited to any particular anion. Accordingly, X can be any suitable counterion that forms a salt with the positively charged thiazolium ion. For instance, in certain aspects of the invention, X can be a halide (e.g., chlorine, bromine). Thus, a person of ordinary skill in the art will recognize that the thiazolium compounds encompassed herein can comprise (or consist essentially of, or consist of) a thiazolium salt.

Similar to R, $R^1$, $R^2$, $R^3$, and $R^4$ discussed and defined hereinabove, $R^5$, $R^6$, and $R^7$ in formula (V) independently can be H, a halide, a $C_1$ to $C_{36}$ hydrocarbyl group, a $C_1$ to $C_{36}$ hydrocarboxy group, a $C_1$ to $C_{36}$ halogenated hydrocarbyl group, a $C_1$ to $C_{36}$ hydrocarbylaminyl group, a $C_1$ to $C_{36}$ hydrocarbylsilyl group, or a $C_1$ to $C_{36}$ hydrocarbylaminylsilyl group. In one aspect, $R^5$, $R^6$, and $R^7$ independently can be H, a $C_1$ to $C_{18}$ hydrocarbyl group, or a $C_1$ to $C_{18}$ hydrocarboxy group, while in another aspect, $R^5$, $R^6$, and $R^7$ independently can be a methyl group, an ethyl group, an n-propyl group, an iso-propyl group, an n-butyl group, a t-butyl group, a phenyl group, a benzyl group, a tolyl group, a xylyl group, a hydroxymethyl group, a hydroxyethyl group, a hydroxypropyl group, or a hydroxybutyl group. A non-limiting example of a thiazolium compound suitable for use in the processes described herein is 3-benzyl-5-(2-hydroxyethyl)-4-methylthiazolium chloride.

The catalyst composition also can comprise a base. While not wishing to be bound by the following theory, contacting a base with a thiazolium compound (or cyanide compound) can result in the formation of an ylide species or a carbene species, which may be primarily responsible for the catalytic effect of the catalyst composition. In certain aspects, the base can comprise an amine (a secondary amine, a tertiary amine, a cyclic amine, an alkylamine, or combinations thereof), a nitrogenous heterocycle, an imine, or combinations thereof. Suitable bases, therefore, can include, but are not limited to, trimethylamine, triethylamine, tri-n-propylamine, diisopropylethylamine, triisopropylamine, tri-n-butylamine, trioctylamine, tridecylamine, triphenylamine, tribenzylamine, pyridine, lutidine, collidine, quinolone, 1,8-diazabicyclo[5.4.0]undec-7-ene, 1,5-diazabicyclo[4.3.0]non-5-ene, and the like. Combinations of more than one base can be utilized. In particular aspects, the catalyst composition can comprise a thiazolium compound and triethylamine, or alternatively, the catalyst composition can comprise a thiazolium compound and 1,8-diazabicyclo[5.4.0]undec-7-ene.

The molar ratio of the base to the thiazolium compound is not particularly limited; typical ranges for the molar ratio of the base to the thiazolium compound can include from about 0.1:1 to about 500:1, from about 0.5:1 to about 100:1, from about 0.1:1 to about 50:1, or from about 1:1 to about 20:1. In some aspects, the amount of the base exceeds the amount of the thiazolium compound, and in these circumstances, the molar ratio of the base to the thiazolium compound often ranges from about 1.5:1 to about 10:1, from about 2:1 to about 15:1, or from about 3:1 to about 10:1.

Similarly, the molar ratio of the thiazolium compound to the α,β-unsaturated carbonyl compound is not particularly limited. Generally, any molar ratio capable of producing the dicarbonyl compound in an acceptable yield can be used. For instance, in certain aspects, the molar ratio of the thiazolium compound to the α,β-unsaturated carbonyl compound can be in a range from about 1:1 to about 1:10,000, from about 1:1 to about 1:1000, from about 1:5 to about 1:1000, from about 1:10 to about 1:1000, from about 1:20 to about 1:1000, from about 1:20 to about 1:500, from about 1:10 to about 1:100, or from about 1:20 to about 1:50.

EXAMPLES

The invention is further illustrated by the following examples, which are not to be construed in any way as imposing limitations to the scope of this invention. Various other aspects, modifications, and equivalents thereof, which after reading the description herein, can suggest themselves to one of ordinary skill in the art without departing from the spirit of the present invention or the scope of the appended claims.

Gas Chromatograph (GC) analyses were conducted on an Agilent 6890 GC System, using a DB-1 column (dimethylpolysiloxane, capillary 2 m×0.25 μm×1 μm nominal), with 40° C. temperature hold for 2 minutes followed by ramping at a rate of 8° C./min from 40° C. to 120° C. Standards for methyl vinyl ketone, 2,5-dimethylpyrrole, and other materials were used to identify the reactants and products, and to monitor the course of the reactions. Product composition information is presented in area percentages (area %), unless otherwise specified.

Examples 1-7

Synthesis of a γ-dicarbonyl Compound (2,5-hexanedione)

The impact of the presence and composition of a diluent on processes to produce γ-dicarbonyl compounds was evaluated in Examples 1-7, which is illustrated by the following reaction scheme:

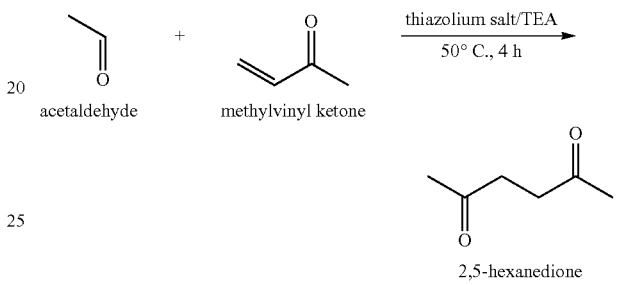

Example 1 was conducted in accordance with the following procedure. To a 3-neck, 1-L round bottom flask equipped with a magnetic stir bar, reflux condenser, thermocouple, addition funnel, and nitrogen inlet and outlet, 3-benzyl-5-(2-hydroxyethyl)-4-methylthiazolium chloride (30 g), a diluent (N-methyl-2-pyrrolidone, 260 mL), methyl vinyl ketone (90% purity, 226 mL), and triethylamine (45 mL) were added under nitrogen. The flask was then cooled in an ice water bath and acetaldehyde (227 mL) was added dropwise over 30 minutes, utilizing the addition funnel. After the acetaldehyde addition, the ice bath was removed and the reaction mixture was allowed to warm to room temperature. After warming, no solids remained in the reaction mixture. After all solids were dissolved, the reaction mixture was transferred to a 1-L autoclave reactor. The autoclave reactor was purged and evacuated with nitrogen 3 times, and 60 psig of nitrogen was charged to the reactor. The reactor was then heated to 50° C. for 4 hours, then cooled to ambient temperature. The components of the crude product mixture were identified and quantified by GC, as detailed in Table I below (the values are in area percentages with the diluent excluded; mole percentages are comparable to the area percentages). The yield of 2,5-hexanedione in Example 1 was 62 area % (~62 mole %). FIG. 1 is a GC plot of the crude product mixture of Example 1, in which the diluent was N-methyl-2-pyrrolidone.

The same general procedure was used for Examples 2-7 with different diluents (or no diluent). The results are summarized in Table II below, with the respective yields of 2,5-hexanedione shown in area percentages with the diluent excluded. As above, the values in mole percentages are comparable to those in area percentages.

Unexpectedly, the yield of 2,5-hexanedione in Example 1 (62%) was at least twice that of any of Examples 2-7. Moreover, the yield of 2,5-hexanedione in Example 1 was three (3) to five (5) times that of Examples 2 and 6, in which alcohol diluents were used instead of N-methyl-2-pyrrolidone.

TABLE I

Composition of Example 1.

| Example | Diluent | Acetoin/ Tri- ethylamine | Acetal- dehyde | Methyl vinyl ketone | 2,5- hex- anedione |
|---|---|---|---|---|---|
| 1 | N-methyl pyrrolidone | 28% | <1% | 9% | 62% |

Summary of Examples 2-7.

| Example | Diluent | Temperature (° C.) | Pressure (psig) | 2,5-hexanedione (yield, area %) |
|---|---|---|---|---|
| 2 | Methanol | 94 | 62 | 20% |
| 3 | Neat (none) | 59 | 160 | 24% |
| 4 | Toluene | 55 | 150 | 19% |
| 5 | Ethyl acetate | 40 | 25 | 27% |
| 6 | Ethanol | 53 | 50 | 13% |
| 7 | Sulfolane | 90 | N/A | 12% |

Example 8

Isolation and Purification of a γ-dicarbonyl (2,5-hexanedione)

Figure 2:
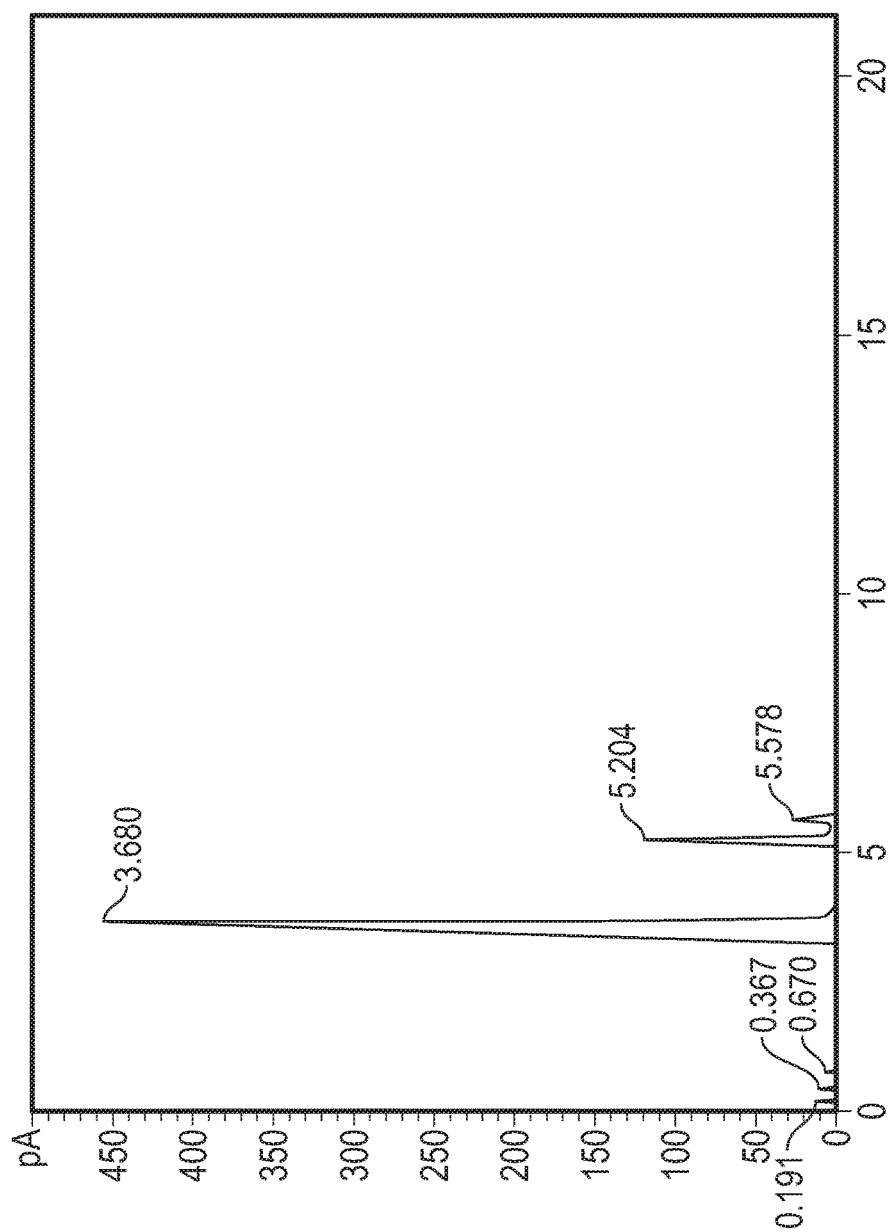
FIG. 2 presents a gas chromatograph plot of the isolated 2,5-hexanedione of Example 8 using vacuum distillation.

Example 8 employed a vacuum distillation of the crude product mixture of Example 1 in accordance with the following procedure. The crude product mixture was heated to reflux slowly under reduced pressure. Initially, a light fraction was taken overhead at 125° C., while slowly decreasing the pressure from 110 torr to 70 torr with a reflux ratio of 5/10. After all lights were removed, the pressure was lowered to 42 torr and the temperature was decreased to 105° C. The reflux ratio was gradually changed to 5/30 as the purity of the overhead product decreased. The recovered product (167 grams) was 91.3% purity 2,5-hexanedione by GC area percentages (see FIG. 2), with N-methylpyrrolidone making up most of the remaining composition. The overall molar yield was 55%, based on the methyl vinyl ketone. Beneficially, it was found that the 2,5-hexanedione was easy to separate from the N-methyl-2-pyrrolidone diluent.

Example 9

Synthesis of a Pyrrole Compound (2,5-dimethylpyrrole) from a γ-dicarbonyl Compound (2,5-hexanedione)

The 2,5-hexanedione (142 g, ~90% purity) was charged into a 250-mL round bottom flask equipped with a stirbar, heating mantle, reflux condenser, and nitrogen inlet and outlet. The reaction flask was heated to 60° C. and ammonium carbonate (150 g) was charged over a period of 90 minutes. Gas evolution was apparent during this heating stage. Once gas evolution stopped, the temperature was increased to 80° C. for 30 minutes. After cooling to room temperature, the two-phase reaction mixture was separated in a separatory funnel. The aqueous phase produced during the reaction was separated from the product and the product was washed with an additional 125 mL of water. A total of 90 grams of 2,5-dimethylpyrrole (85% molar yield, based on the dione) were collected at a purity, as determined by GC analysis, of 96 area % (approximately 96 mole %).

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A process for producing a pyrrole compound having formula (IV):

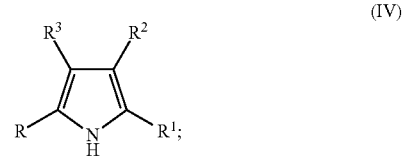

the process comprising:
(1) contacting:
(a) an aldehyde compound having formula (II),

(b) an α,β-unsaturated carbonyl compound having formula (III),

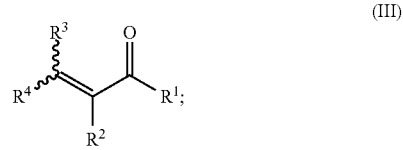

and
(c) a catalyst composition;
in an amide diluent to produce a γ-dicarbonyl compound having formula (I),

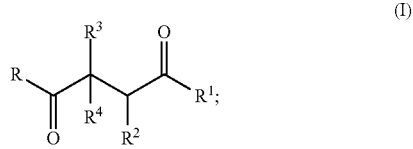

and
(2) contacting the γ-dicarbonyl compound with ammonia or an ammonium salt to produce the pyrrole compound; wherein:
R, $R^1$, $R^2$, and $R^3$ independently are H, a halide, a $C_1$ to $C_{36}$ hydrocarbyl group, a $C_1$ to $C_{36}$ hydrocarboxy group, a $C_1$ to $C_{36}$ halogenated hydrocarbyl group, a $C_1$ to $C_{36}$ hydrocarbylaminyl group, a $C_1$ to $C_{36}$ hydrocarbylsilyl group, or a $C_1$ to $C_{36}$ hydrocarbylaminylsilyl group; and $R^4$ is H.

Aspect 2. The process defined in aspect 1, wherein step (2) comprises contacting the γ-dicarbonyl compound with ammonia (e.g., liquid or gaseous ammonia).

Aspect 3. The process defined in aspect 1 or 2, wherein step (2) comprises contacting the γ-dicarbonyl compound with an ammonium salt (e.g., ammonium carbonate, ammonium acetate).

Aspect 4. A process for producing a γ-dicarbonyl compound having formula (I),

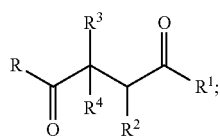

the process comprising contacting:
(a) an aldehyde compound having formula (II),

(b) an α,β-unsaturated carbonyl compound having formula (III),

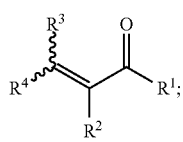

and
(c) a catalyst composition;
in an amide diluent to produce the γ-dicarbonyl compound; wherein:
R, $R^1$, $R^2$, $R^3$, and $R^4$ independently are H, a halide, a $C_1$ to $C_{36}$ hydrocarbyl group, a $C_1$ to $C_{36}$ hydrocarboxy group, a $C_1$ to $C_{36}$ halogenated hydrocarbyl group, a $C_1$ to $C_{36}$ hydrocarbylaminyl group, a $C_1$ to $C_{36}$ hydrocarbylsilyl group, or a $C_1$ to $C_{36}$ hydrocarbylaminylsilyl group.

Aspect 5. The process defined in aspect 4, wherein R, $R^1$, $R^2$, $R^3$, and $R^4$ independently are H, a $C_1$ to $C_{18}$ hydrocarbyl group, a $C_1$ to $C_{18}$ hydrocarboxy group, or a $C_1$ to $C_{18}$ halogenated hydrocarbyl group.

Aspect 6. The process defined in aspect 4 or 5, wherein R, $R^1$, $R^2$, $R^3$, and $R^4$ independently are H or a $C_1$ to $C_{18}$ hydrocarbyl group.

Aspect 7. The process defined in any one of aspects 4-6, wherein R, $R^1$, $R^2$, $R^3$, and $R^4$ independently are H or a $C_1$ to $C_{18}$ alkyl, aryl, or arylalkyl group.

Aspect 8. The process defined in any one of aspects 4-7, wherein $R^4$ is H.

Aspect 9. The process defined in any one of aspects 1-8, wherein R and $R^1$ independently are a $C_1$-$C_{18}$ hydrocarbyl group, and $R^2$ and $R^3$ are hydrogen.

Aspect 10. The process defined in any one of aspects 1-9, wherein R and $R^1$ independently are a methyl group, an ethyl group, an n-propyl group, an iso-propyl group, an n-butyl group, a t-butyl group, a phenyl group, a benzyl group, a tolyl group, or a xylyl group.

Aspect 11. The process defined in any one of aspects 1-10, wherein R is methyl.

Aspect 12. The process defined in any one of aspects 1-11, wherein R and $R^1$ are a methyl group, and $R^2$ and $R^3$ are hydrogen.

Aspect 13. The process defined in any one of aspects 1-12, wherein the amide diluent comprises a cyclic amide (e.g., a lactam, pyrrolidone, N-methylpyrrolidone) and/or a hydrocarbyl amide (e.g., acetamide, dimethylacetamide, dimethylformamide, benzamide, pyrrolidone, N-methylpyrrolidone).

Aspect 14. The process defined in any one of aspects 1-13, wherein the amide diluent comprises a secondary amide (e.g., pyrrolidone) or a tertiary amide (e.g., N-methylpyrrolidone).

Aspect 15. The process defined in any one of aspects 1-14, wherein the catalyst composition comprises a carbene species, an ylide species, and/or a cyanide compound.

Aspect 16. The process defined in any one of aspects 1-15, wherein the catalyst composition comprises:
a thiazolium compound having formula (V):

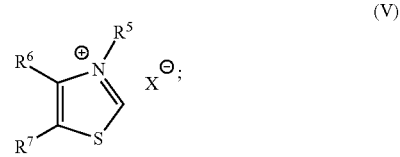

and
a base; wherein:
$R^5$, $R^6$, and $R^7$ independently are H, a $C_1$ to $C_{36}$ hydrocarbyl group, a $C_1$ to $C_{36}$ hydrocarboxy group, a $C_1$ to $C_{36}$ halogenated hydrocarbyl group, a $C_1$ to $C_{36}$ hydrocarbylaminyl group, a $C_1$ to $C_{36}$ hydrocarbylsilyl group, or a $C_1$ to $C_{36}$ hydrocarbylaminylsilyl group; and
X is a halogen.

Aspect 17. The process defined in aspect 16, wherein the thiazolium compound forms an ylide species in the presence of the base.

Aspect 18. The process defined in aspect 16 or 17, wherein $R^5$, $R^6$, and $R^7$ independently are H, a $C_1$ to $C_{18}$ hydrocarbyl group, or a $C_1$ to $C_{18}$ hydrocarboxy group.

Aspect 19. The process defined in any one of aspects 16-18, wherein $R^5$, $R^6$, and $R^7$ independently are a methyl group, an ethyl group, an n-propyl group, an iso-propyl group, an n-butyl group, a t-butyl group, a phenyl group, a benzyl group, a tolyl group, a xylyl group, a hydroxymethyl group, a hydroxyethyl group, a hydroxypropyl group, or a hydroxybutyl group.

Aspect 20. The process defined in any one of aspects 16-19, wherein the thiazolium compound comprises a thiazolium salt.

Aspect 21. The process defined in any one of aspects 16-20, wherein the thiazolium compound comprises 3-benzyl-5-(2-hydroxyethyl)-4-methylthiazolium chloride.

Aspect 22. The process defined in any one of aspects 16-21, wherein the base comprises an amine (e.g., a tertiary amine, an alkylamine, trimethylamine, triethylamine, tri-n-propylamine, diisopropylethylamine, triisopropylamine, tri-n-butylamine, trioctylamine, tridecylamine, triphenylamine, tribenzylamine, etc.), a nitrogenous heterocycle (e.g., pyridine, lutidine, collidine, quinolone, etc.), and/or an imine base (e.g., 1,8-diazabicyclo[5.4.0]undec-7-ene, 1,5-diazabicyclo[4.3.0]non-5-ene, etc.).

Aspect 23. The process defined in any one of aspects 16-22, wherein a molar ratio of the base to the thiazolium compound is in a range from about 1:1 to about 20:1, from about 2:1 to about 15:1, or from about 3:1 to about 10:1.

Aspect 24. The process defined in any one of aspects 16-23, wherein the molar ratio of the thiazolium compound to the α,β-unsaturated carbonyl compound is in a range from about 1:5 to about 1:1000, from about 1:10 to about 1:100, or from about 1:20 to about 1:50.

Aspect 25. The process defined in any one of aspects 1-24, wherein the molar ratio of the aldehyde compound to the α,β-unsaturated carbonyl compound is greater than about 1:1, greater than about 1.2:1, or in a range from about 1:1 to about 2:1.

Aspect 26. The process defined in any one of aspects 1-25, wherein the α,β-unsaturated carbonyl compound is a limiting reactant in the production of the γ-dicarbonyl compound.

Aspect 27. The process defined in any one of aspects 1-26, wherein a volumetric ratio of the amide diluent to the α,β-unsaturated carbonyl compound is in a range from about 1:2 to about 10:1, or from about 1:1.5 to about 1.5:1.

Aspect 28. The process defined in any one of aspects 1-27, wherein the step of contacting the aldehyde compound, the α,β-unsaturated carbonyl compound, and the catalyst composition in the amide diluent is conducted at a temperature in a range from about −20° C. to about 70° C.

Aspect 29. The process defined in any one of aspects 1-28, wherein the step of contacting the aldehyde compound, the α,β-unsaturated carbonyl compound, and the catalyst composition in the amide diluent is conducted for a time period of from about 5 minutes to about 8 hours.

Aspect 30. The process defined in any one of aspects 1-29, wherein the step of contacting the aldehyde compound, the α,β-unsaturated carbonyl compound, and the catalyst composition in the amide diluent comprises contacting the aldehyde compound, the α,β-unsaturated carbonyl compound, the catalyst composition, and the amide diluent in any order.

Aspect 31. The process defined in any one of aspects 1-30, wherein the step of contacting the aldehyde compound, the α,β-unsaturated carbonyl compound, and the catalyst composition in the amide diluent comprises:
contacting the α,β-unsaturated carbonyl compound, the catalyst composition, and the amide diluent to form a reactant mixture; and
contacting the aldehyde compound with the reactant mixture.

Aspect 32. The process defined in any one of aspects 1-31, wherein the γ-dicarbonyl compound is produced in a yield of at least about 40 mole %, at least about 50 mole %, at least about 60 mole %, or at least about 70 mole %, based on the α,β-unsaturated carbonyl compound.

Aspect 33. The process defined in any one of aspects 1-32, further comprising a step of isolating the γ-dicarbonyl compound.

Aspect 34. The process defined in aspect 33, wherein isolating comprises an extraction step.

Aspect 35. The process defined in aspect 33 or 34, wherein isolating comprises a distillation step at atmospheric pressure or any suitable sub-atmospheric pressure.

Aspect 36. The process defined in any one of aspects 33-35, wherein the isolated γ-dicarbonyl compound is recovered in a yield of at least about 40 mole %, at least about 50 mole %, at least about 60 mole %, or at least about 70 mole %, based on the α,β-unsaturated carbonyl compound.

Aspect 37. The process defined in any one of aspects 33-36, wherein a purity of the isolated γ-dicarbonyl compound is at least about 80 mole %, at least about 85 mole %, at least about 90 mole %, or at least about 95 mole %.

I claim:
1. A process for producing a γ-dicarbonyl compound having formula (I),

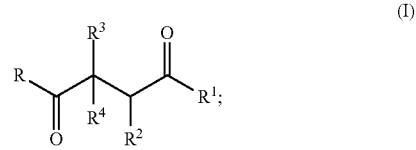

the process comprising contacting:
(a) an aldehyde compound having formula (II),

(b) an α,β-unsaturated carbonyl compound having formula (III),

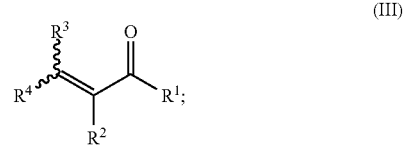

and
(c) a catalyst composition;
in an amide diluent to produce the γ-dicarbonyl compound; wherein:
R, $R^1$, $R^2$, $R^3$, and $R^4$ independently are H, a halide, a $C_1$ to $C_{36}$ hydrocarbyl group, a $C_1$ to $C_{36}$ hydrocarboxy group, a $C_1$ to $C_{36}$ halogenated hydrocarbyl group, a $C_1$ to $C_{36}$ hydrocarbylaminyl group, a $C_1$ to $C_{36}$ hydrocarbylsilyl group, or a $C_1$ to $C_{36}$ hydrocarbylaminylsilyl group.

2. The process of claim 1, wherein the amide diluent comprises a cyclic amide.

3. The process of claim 1, wherein the amide diluent comprises a hydrocarbyl amide.

4. The process of claim 1, wherein the amide diluent comprises a secondary amide and/or a tertiary amide.

5. The process of claim 1, wherein the amide diluent comprises pyrrolidone, N-methylpyrrolidone, a lactam, acetamide, dimethylacetamide, dimethylformamide, benzamide, or any combination thereof.

6. The process of claim 1, wherein R, $R^1$, $R^2$, $R^3$, and $R^4$ independently are H, a $C_1$ to $C_{18}$ hydrocarbyl group, a $C_1$ to $C_{18}$ hydrocarboxy group, or a $C_1$ to $C_{18}$ halogenated hydrocarbyl group.

7. The process of claim 1, wherein:
$R^4$ is H;
R and $R^1$ independently are a $C_1$ to $C_{18}$ hydrocarbyl group; and
$R^2$ and $R^3$ are hydrogen.

8. The process of claim 7, wherein R and $R^1$ are a methyl group.

9. The process of claim 1, wherein the process comprises:
contacting the α,β-unsaturated carbonyl compound, the catalyst composition, and the amide diluent to form a reactant mixture; and contacting the aldehyde compound with the reactant mixture.

10. The process of claim 1, wherein the γ-dicarbonyl compound is produced in a yield of at least about 50 mole %, based on the α,β-unsaturated carbonyl compound.

11. The process of claim 1, wherein:
a molar ratio of the aldehyde compound to the α,β-unsaturated carbonyl compound is in a range from about 1:1 to about 2:1;
a volumetric ratio of the amide diluent to the α,β-unsaturated carbonyl compound is in a range from about 1:2 to about 5:1; and
the γ-dicarbonyl compound is produced in a yield of at least about 50 mole %, based on the α,β-unsaturated carbonyl compound.

12. The process of claim 1, further comprising a step of isolating the γ-dicarbonyl compound at a purity of at least about 85 mole %.

13. The process of claim 1, wherein the catalyst composition comprises a carbene species, an ylide species, and/or a cyanide compound.

14. The process of claim 1, wherein the catalyst composition comprises a thiazolium compound and a base.

15. The process of claim 14, wherein a molar ratio of the thiazolium compound to the α,β-unsaturated carbonyl compound is in a range from about 1:10 to about 1:100.

16. The process of claim 14, wherein:
a molar ratio of the base to the thiazolium compound is in a range from about 1:1 to about 20:1; and
the base comprises an amine, a nitrogenous heterocycle, an imine, or any combination thereof.

17. A process for producing a pyrrole compound having formula (IV):

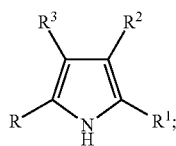

(IV)

the process comprising:
(1) contacting:
(a) an aldehyde compound having formula (II),

(II)

(b) an α,β-unsaturated carbonyl compound having formula (III),

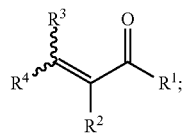

(III)

and
(c) a catalyst composition;
in an amide diluent to produce a γ-dicarbonyl compound having formula (I),

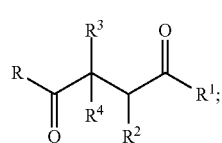

(I)

and
(2) contacting the γ-dicarbonyl compound with ammonia or an ammonium salt to produce the pyrrole compound;
wherein:
R, $R^1$, $R^2$, and $R^3$ independently are H, a halide, a $C_1$ to $C_{36}$ hydrocarbyl group, a $C_1$ to $C_{36}$ hydrocarboxy group, a $C_1$ to $C_{36}$ halogenated hydrocarbyl group, a $C_1$ to $C_{36}$ hydrocarbylaminyl group, a $C_1$ to $C_{36}$ hydrocarbylsilyl group, or a $C_1$ to $C_{36}$ hydrocarbylaminylsilyl group; and
$R^4$ is H.

18. The process of claim 17, wherein:
the amide diluent comprises pyrrolidone, N-methylpyrrolidone, a lactam, acetamide, dimethylacetamide, dimethylformamide, benzamide, or any combination thereof;
R and $R^1$ independently are a $C_1$ to $C_{18}$ hydrocarbyl group; and
$R^2$ and $R^3$ are hydrogen.

19. The process of claim 18, wherein R and $R^1$ are a methyl group.

20. The process of claim 17, wherein:
prior to step (2), the process further comprises a step of isolating the γ-dicarbonyl compound at a purity of at least about 85 mole %; and
the step of isolating comprises an extraction step and/or a distillation step.

\* \* \* \* \*